United States Patent [19]
Langlois et al.

[11] Patent Number: 6,156,163
[45] Date of Patent: Dec. 5, 2000

[54] REACTANT, COMPOUND AND PROCESS FOR THE PERFLUOROALKYLATION OF THE NUCLEOPHILE, AND THE DERIVATIVES OBTAINED

[75] Inventors: Bernard Langlois, Lyons; Nicolas Roques, Sete; Claude Wakselman, Paris; Marc Tordeux, Sceaux; Gérard Forat, Lyons, all of France

[73] Assignee: Rhodia Chimie, Courbevoie, France

[21] Appl. No.: 08/894,392

[22] PCT Filed: Feb. 19, 1996

[86] PCT No.: PCT/FR96/00264

§ 371 Date: Nov. 6, 1997

§ 102(e) Date: Nov. 6, 1997

[87] PCT Pub. No.: WO96/26185

PCT Pub. Date: Aug. 29, 1996

[30] Foreign Application Priority Data

Feb. 24, 1995 [FR] France ................................ 95 02157
Sep. 15, 1995 [FR] France ................................ 95 10937

[51] Int. Cl.[7] .................... C07F 1/00; C07C 17/00; C07C 17/26; C09K 3/00
[52] U.S. Cl. .................... 204/157.6; 204/157.76; 204/157.78; 204/157.79; 204/157.8; 204/157.94; 204/158.11; 204/158.12; 252/183.11; 252/600; 570/171; 570/175; 588/230; 588/250
[58] Field of Search ................ 204/157.6, 157.76, 204/157.78, 157.79, 157.8, 157.94, 158.11, 158.12; 252/183.11, 600; 570/171, 175; 588/230, 250

[56] References Cited

FOREIGN PATENT DOCUMENTS 307519    3/1989   European Pat. Off. .
458684   11/1991   European Pat. Off. .

OTHER PUBLICATIONS

Brookes et al., "Reactions of Fluoroalkyl Radicals Generated Electrochemically. Part I. Additions of Trifluoromethyl Radicals to Olefinic and Acetylenic Bonds", J. Chem. Soc., No. 3, pp. 202–209, 1978.

Clavel et al., "Trifluoromethylation of Organic Disulphides With Sodium Trifluoromethane–Sulphinate Under Oxidative Conditions: Synthesis of Trifluoromethyl Thioethers", Phosphorus, Sulfur, Silicon and the Related Elements, vol. 59, Nos. 1–4, pp. 169–172, 1991.

Bock et al., "Study of d–Orbital Effects in Esters of Trifluorothiolacetic Acid. A Comparison of Evidence From Dipole Moment and Kinetic Data", Can. J. Chem., vol. 52, No. 17, pp. 3113–3118, Sep. 1974.

Weeks et al., "Chemistry of Trifluorothiolacetic Acid and Its Derivatives. II", J. Fluorine Chem., vol. 1, No. 3, pp. 295–307, Jan. 1972.

Haszeldine et al., "The Reactions of N,N–bistrifluoromethylaminotrifluoromethanesulphonate With Nucleophiles", J. Fluorine Chem., vol. 8, No. 1, pp. 101–104, 1976.

DeMarco et al., "Reactions of the Difluoroamine–Potassium Fluoride Adduct, HNF2.KF, With Sulphinyl and Perfluoroalkylsulphinylfluorides. Preparation of Perfluoroalkyl Perfluoroalkylsulphinates", Inorg. Chem., vol. 12, No. 8, pp. 1896–1899, Aug. 1973.

Bzhezovskii et al., "13C NMR and X–ray Fluorescence Spectra of a Series of Benzyl Sulphides", Bull. of the Academy of Sci. of the USSR, vol. 34, No. 6, Part 2, pp. 1281–1283, Jun. 1985.

Nguyen et al., "Perfluorothioalkanoyl Halides. Preparation From Sulphides", J. Fluorine Chem., vol. 35, No. 3, pp. 523–530, Mar. 1987.

*Primary Examiner*—Kathryn Gorgos
*Assistant Examiner*—Edna Wong
*Attorney, Agent, or Firm*—Jean-Louis Seugnet

[57] ABSTRACT

A reagent comprising a compound of formula (I): $R_f$—M(X)(Z)$_n$—Y—R, wherein R is a hydrocarbon radical advantageously having at most 10 carbon atoms and being selected from alkyls and aryls; $R_f$ is a radical of formula II: $R_1$—(CΞ$_2$)$_m$—CF$_2$—, where $R_1$ is a fluorine or chlorine atom or a carbon radical, m is 0 or a integer from 0–12, and each Ξ, which may be the same or different, is a chlorine or preferably fluorine atom, with the proviso that when m is 0, $R_1$ is electroattractive, preferably a fluorine atom; n is 0 or 1; M is a non-metal selected from carbon and chalcogens with an atomic number higher than oxygen; and each of X, Y and Z, which are the same or different, is a chalcogen; as well as a generator, for consecutive or simultaneous addition. The reagent is useful for organic synthesis.

16 Claims, No Drawings

REACTANT, COMPOUND AND PROCESS FOR THE PERFLUOROALKYLATION OF THE NUCLEOPHILE, AND THE DERIVATIVES OBTAINED

This application is an application under 35 U.S.C. Section 371 of International Application No. PCT/FR96/00264, filed on Feb. 19, 1996.

The present invention relates to a perfluoroalkylation technique and especially a reactant, a compound and a process for the perfluoroalkylation of a nucleophile, and to the derivatives thus obtained. It relates more particularly to the use of the homolytic scission of certain chalcogen esters with relatively heavy chalcogens, that is to say of an atomic row at least equal to that of sulphur.

Thus, the field of the invention is that of the synthesis of compounds which are perhaloalkylated and/or acylated;
either by grafting of perhaloalkyl and/or acyl radicals on to substrates, at least partially organic and of various kinds, the said radicals being supplied by perhaloalkylating and/or acylating agents,
or by direct autotransformation of perhaloalkylating agents.

The present invention also relates to a process for obtaining perhalogenated, in particular perhaloalkylated and/or acylated compounds and to perhaloalkylated and/or acylated thioethers.

The halogen considered more precisely but without any limitation being implied is fluorine, because of the great interest which exists in employing it is a substituent in many industrial products such as colorants, polymers and pharmaceutical and agrochemical compounds. It is well known, in fact, that fluorine is an inducer of lipophilicity in biologically active molecules.

Moreover its electronegativity and its relatively small size are positive factors in relation to:
the absorption of light by colorants,
the stability, solubility and mechanical and electrical properties of polymers,
and the biological properties of certain pharmaceutical and/or agrochemical molecules.

Bearing in mind the scientific and technical interest of the trifluoromethyl substituent, especially in the pharmaceutical and the agrochemical fields, many methods of trifluoromethylation have already been proposed.

Among these, direct trifluoromethylation according to an electrophilic, nucleophilic and/or radical mechanism is that most worthy of interest from the technical and industrial standpoint.

Techniques for trifluoromethylation by a radical have the advantage of often making it possible to operate in very mild conditions.

To be sure, using this route, the perfluoroalkylation with the aid of perfluoroalkyl iodides such as $CF_3I$ is known. These compounds react with various substrates thermally, under irradiation or in the presence of a catalytic quantity of a radical initiator such as benzoyl peroxide or azobisiobutyronitrile (AIBN). Perfluoroalkyl iodides are costly products and rarely available on an industrial scale.

Moreover, the reactions involved are liable to give rise, as by-products, to iodine-containing products known to be toxic, of the $CF_3$—$CH_2$—$CH_2$—I type.

Derivatives of perfluoroalkanesulphonic acids which are also suitable for a radical route are themselves also costly and still rarely available on an industrial scale.

Nitrosotrifluoromethane derivatives can also be employed, but suffer from the disadvantage of being toxic and hazardous to synthesize.

Perfluoroalkanoic acids and their derivatives, such as trifluoroacetic acid, could possibly have been employed as perhaloalkylating agents. It has been found, however, that they are difficult to convert into the $.CF_3$ radical. The electrochemical oxidation used for this purpose requires, in fact, very high voltages and large excesses of this reactant. The industrial feasibility of the process involving these compounds is therefore not established.

Trifluoromethanethiol ($CF_3SH$) and trifluoromethanesulphenyl chloride $CF_3SCl$ are known as being reactive agents for trifluoromethylthioalation. However, they have the disadvantage of being gaseous and highly toxic.

In practice, the most common trifluoromethylating agent is bromotrifluoromethane ($CF_3Br$). This industrial product is employed a fire-extinguishing agent, especially in aircraft and computer rooms. It is at present one of the largest sources of trifluoromethyl radicals.

$CF_3Br$ can be reduced monoelectronically to give $.CF_3$, a radical capable of being trapped, either by nucleophilic substrates, reducing agents and initiators, such as thiolates, thiophenates, selenophenates, stabilized carbanions or enamines, or by a reducing agent of the $SO_2^-$. Type.

By way of example of a conversion, according to the abovementioned technique, of disulphide substrates giving rise to trifluoromethylated alkyls or aryl sulphides, reference will be made to the paper by Clavel et al.: *Phosphorus, Sulfur & Silicon*, 1991, vol. 59, p. 129–132. The paper of Wakselman et al., *J. Chem. Soc., Chem. Commun.*, 1984, p. 793–794, gives an illustration of the trifluoromethylation of thiophenols with the aid of $CF_3Br$.

Alternatively, $.CF_3$ can be generated with the aid of an oxidizing agent of the tert-butyl hydroperoxide (t—BuOOH) type and of sodium trifluoromethanesulphinate ($CF_3SO_2Na$), itself obtained from bromotrifluoromethane and sodium dithionite. In these conditions disulphides are converted to trifluoromethyl thioethers ($RSCF_3$) (cf. Clavel & al.: *Phosphorus, Sulfur & Silicon*, 1991, vol. 59, pages 169–172), aromatic compounds are trifluoromethylated (cf. Langlois & al.: *Tetrahedron Letters*, 1991, vol. 32, No. 51, p. 7525–7528) and enol esters produce trifluoromethyl ketones (cf. Langlois & al.: *Tetrahedron Letters*, 1992, vol. 33, No. 10, p. 1291–1294).

The problem related to these known techniques employing bromotrifluoromethane as source of $.CF_3$ has to do with the difficulty of handling this gas. What is more, it is a product which is bound to be prohibited by the international regulations dealing with the environment, because of its presumed harmful effects on the environment, especially because of the greenhouse effect which it allegedly produces, the hypothetical effects on the ozone layer.

This will therefore give rise to a considerable demand for radical trifluoromethylating agents which are convenient to use, nontoxic, easily available and inexpensive.

Thus, one of the objectives of the present invention is to provide a process for obtaining perhalogenated, in particular perhaloalkylated and/or acylated, compounds in which advantageous substitutes for bromotrifluoromethane are used.

Another aim of the present invention is to provide a reaction of the above type which allows a perfluoro radical to be grafted on to an electrophile.

Another aim of the present invention is to provide compounds which are capable of being employed for the above reactants and/or in the above process.

Another aim of the present invention is to provide derivatives which are capable of being obtained by the reactants and process of the above type.

The Applicant company has succeeded in developing such a reactant, which is characterized in that it comprises, for successive or simultaneous addition:

a compound of formula (I):

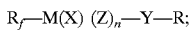

with R denoting a carbon-containing radical, advantageously of at most 15 preferably 10 carbon atoms, preferably chosen from alkyls, aryls, acyls, thioacyls [such as the hydrocarbylchalcogenylacyls (and especially carbonyls) (the preferred chalcogens here are sulphur and oxygen), especially aryloxyacyls, alkoxyacyls and in particular aryloxycarbonyls, alkoxycarbonyls and aryloxythiocarbonyls, alkoxythiocarbonyls or their homologues when the oxygens are completely or partially replaced with sulphur];

with $R_f$, advantageously exhibiting at most 20 carbon atoms, preferably at most 15 carbon atoms, denoting a radical of formula (II):

where $R_1$ and $R_2$, which are similar or different, denote a light halogen atom, fluorine or chlorine, preferably fluorine, a carbon-containing radical where m is zero or an integer chosen within the closed interval from 0 to 12, advantageously at most equal to 8 and preferably at most equal to 6;

where p is zero or an integer chosen within the closed interval from 0 to 12, advantageously at most equal to 6, preferably at most equal to 4;

where the Ξs, which are similar or different, denote perhalogenated, advantageously perfluorinated, radicals, chlorine or preferably fluorine atoms; with the condition that when m and/or p are equal to zero, $R_1$ is electron-withdrawing, advantageously a fluorine or chlorine atom, preferably a fluorine atom;

with n denoting zero or 1;

with M denoting a metalloid chosen from carbon and the chalcogens of a row higher than oxygen;

with X, Y and Z, which are similar or different, denoting a chalcogen;

a source of radicals.

When M is carbon n is equal to zero.

Thus R is advantageously a substituted or unsubstituted, linear or branched aliphatic or alicyclic radical, preferably alkyl, including aralkyl, aralkenyl, aralkynyl, alkenyl and alkynyl, and aryl.

R may also be a radical of formula $R_f$—M(X) (Z)$_n$— where $R_f$, M, X, Y, Z and n have the same meaning as set out above, without this meaning that the molecule is necessarily symmetrical.

It is advantageous that X, Y and, when n is other than zero, Z are not all oxygens in the same single molecule.

It should be remembered that the expression "hydrocarbylchalcogenyl" is a radical of structure $R_a$—Y"— where $R_a$— is a hydrocarbon radical, that is to say one containing at least hydrogen and carbon and in which the atom carrying the bond (here with Y") is a carbon, and where Y" is a chalcogen (oxygen, sulphur, selenium, tellurium). $R_a$ is advantageously an alkyl [optionally substituted and especially halogenated (including perhalogenated and especially perfluorinated)] or an optionally substituted aryl.

According to the present invention, if the intention is to avoid interfering reactions, it is highly desirable that R should be chosen so that the radical R· is only slightly stable or unstable; thus, benzyls, tertiary alkyls and any radical whose corresponding free radical is equally, or more, stable than those mentioned above, are to be avoided.

The compounds of formula (I) may be employed in such a way and in such conditions that they, and especially the thioloesters of formula (I), can generate free radicals.

The said radical-generator may be an actinic source. The process according to the invention consists in reacting the thioloesters of formula (I) with an at least partially organic unsaturated substrate, preferably under irradiation at a wavelength of between 200 and 800 nanometers; the said radical-generator is then a source of radiation of wavelength included between 200 and 800 nm and preferably between 210 and 600 nm (nanometers). To obtain the best results it is recommended to adopt the wavelength corresponding to the absorption maximum of the chromophore functional group —M(X) (Z)$_n$ Y—.

The said radical-generator may also be a chemical source of free radicals. As already mentioned above, it is possible to employ the compounds of formula (I) in such a way and in such conditions that they, and especially the thioloesters of formula (III), can generate free radicals.

According to an advantageous method of the invention, the said mechanisms involve an initiator, which may be of chemical nature [for example acyl peroxides, being symmetrical, mixed and/or hydrogen peroxides (the most common of which is the benzoyl compound), alkyl peroxides (in general tertiary, the most widely employed of which are the tert-butyl compounds), or azo derivatives (such as azobisisobutyronitrile=AIBN)], advantageously in the presence of stannane (especially hydrostannane) and/or of silanes (especially hydrosilane); the stannanes and especially the distannanes (such as Bu$_3$SnSnBu$_3$) may be employed alone.

Advantageously the reactant additionally comprises a solvent.

The solvent may also consist of an excess of one of the reactants.

When actinic initiation is employed, to prevent the radiation energy hv initiating the radical reaction from being absorbed by the solvent at the expense of the thioloester (I), it is important to choose the solvent so that it has a transmittance higher than or equal to 50%, preferably to 70%, and, still more preferably, to 90%, at the working wavelength.

Accordingly, in accordance with the invention, when actinic initiation is present, the solvent is preferably selected from the following compounds: acetonitrile, ethanol, butanol, dichloromethane, cyclohexane, cyclopentane, 1,2-dichloroethane, 2,2-dimethylbutane, n-heptane, n-hexane, methanol, 2-methylbutane, isooctane, n-pentane, 2-propanol, 1,2,2-trichlorotrifluoroethane, 2,2,2-trifluoroethanol or a mixture of these.

When another kind of initiation is employed it is appropriate to employ solvents which are inert towards the compounds (I) as in all cases, but also towards initiators that may be physical (radiation, temperature for thermolysis radicals produced from chemical initiators).

If attention is now turned to the compounds of formula (I):

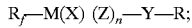

It is desirable that at least one, preferably two compatible conditions hereinafter should be fulfilled:

Y should be a heavy chalcogen advantageously chosen from selenium and sulphur, preferably a sulphur;

Z is a light chalcogen advantageously chosen from oxygen and sulphur, preferably a sulphur;

X is a light chalcogen advantageously chosen from oxygen and sulphur, preferably oxygen;

M is a carbon atom, n is zero, X is oxygen and Y is sulphur or selenium;

M is a sulphur or selenium atom, n is one, X is oxygen and Y is sulphur or selenium.

It is advantageous that X, Y and, when n is other than zero, Z should not all be oxygen in the same single molecule.

Thus, in the course of the study which led to the present invention, it was found that some of the compounds which may be used in the reactant described above had never been described, have had to be synthesized and were new.

Thus, another aim of the present invention is to provide a compound of the above type, as well as a process for the synthesis of these compounds. These aims and others which will appear below are met by means of compound(s) of formula (I)

$$R_f—M(X)(Z)_n—Y—R;$$

with R denoting a hydrocarbon radical, advantageously of at most 10 carbon atoms, preferably chosen from alkyls and aryls;

with $R_f$ denoting a radical of formula:

where $R_1$ and $R_2$, which are similar or different, denote a light halogen atom, fluorine or chlorine, preferably fluorine, a carbon-containing radical where m is zero or an integer included between 0 and 12;
where p is zero or an integer included between 0 and 12;
where the Ξ, which are similar or different, denote perhalogenated, advantageously perfluorinated radicals, chlorine or preferably fluorine atoms; on the condition that when m and/or are equal to zero, $R_1$ is electron-withdrawing, advantageously a fluorine or chlorine atom, preferably a fluorine atom;
with n denoting zero or 1;
with M denoting a metalloid chosen from carbon and the chalcogens of a row higher than oxygen;
with Y denoting a sulphur or a selenium;
with X and Z, which are similar or different, denoting a chalcogen.
$R_1$ is a carbon-containing radical chosen from alkyls and aryls.
$R_f$ is a carbon-containing radical of at most 20 carbons, preferably of at most 15 carbons.

The compounds according to the present invention are particularly advantageous where their $R_f$ comprise(s) more than one carbon atom and, above all, more than three.

It is desirable that there should be at least one chalcogen heavier than oxygen among M and X.

The compounds which have at least one selenium atom as M, X, Y, Z are particularly original. The compounds where M is a chalcogen and where n is equal to 1 have the characteristic of giving only one perfluoroalkylation, which is an advantage when it is this reaction that is required. Finally, the derivatives where R corresponds to the formula $R_f—M(X)(Z)_n—$ are particularly advantageous.

Another aim of the present invention is to provide a process which can be used for grafting perhalogenated, advantageously perfluorinated groups of the above $R_f$ type. This graft may be an autograft, that is to say a graft on a substrate consisting of a compound or a decomposition product of a compound of formula (I):

$$R_f—M(X)(Z)_n—Y—R;$$

This aim and others which will appear in what follow are met by means of a process comprising at least one stage in which the said compound exhibiting at least one nucleophilic functional group is placed in contact with a reactant described above.

The process according to the invention will be described further by frequently employing the thioloesters as a paradigm. These thioloesters are perfluoro compounds which have the following formula:

$$R_f—CO—S—R \qquad (III)$$

in which:

$R_f$ is defined above and advantageously denotes the radical:

where n is at least equal to 1, often equal to 1, and R is a substituted or unsubstituted, linear or branched aliphatic or alicyclic radical, preferably alkyl including alkenyl, alkynyl, aryl, aralkyl, aralkenyl or aralkynyl.

It is practical that the starting materials, according to the invention, should consist of compounds of $CF_3COSR$ type, because these are compounds that are very easily accessible from trifluoroacetic anhydride and a thiol RSH.

In addition, the process according to the invention does not involve the handling of hazardous and toxic products, nor does it generate them.

This perhalo, preferably perfluoro thioloester can be likened to a supplier of the radical $R_f$, often corresponding to $[C_nF_{(2n+1)}]$ for obtaining the compounds which are aimed at.

The process according to invention can especially be envisaged according to two main routes:

the first of these can be summarized as a direct radical conversion of a compound of formula (I) and especially the thioloester (III) to a perfluoroalkyl thioether (or S-alkyl perfluoro compound) $(C_nF_{(2n+1)}—S—R)$, by decarbonylation (or desulphonylation or equivalents).

the second consists essentially in reacting, by a radical route, a compound of formula (I) and especially the thioloester (III) with at least one substrate, in such a way that at least one $C_nF_{(2n+1)}$ and/or $C_nF_{(2n+1)}CO$ radical is grafted onto the said substrate.

In accordance with an advantageous method of the invention, the said mechanisms involve an initiator, which may of chemical nature (e.g. benzoyl. peroxide, tert-butyl peroxide, stannanes such as $Bu_3SnSnBu_3$ or azobisisobutyronitrile=AIBN) and/or of physical nature (thermal route and/or irradiation).

In the case of both routes of the process according to the invention a preferred embodiment consists of a thermolysis of the compound (I) between, preferably, 350 and 650° C. (and more preferably 400 to 600° C.) in, for example, an iron, quartz or glass tube (optionally filled with crushed glass).

In the case of both routes of the process according to the invention, another preferred embodiment consists of a photolysis in a reaction medium optionally containing an organic solvent, at a wavelength and at a reaction temperature $T_R$; is, advantageously, included between 200 and 800 nm and, preferably, between 210 and 600 nm.

To prevent the radiation energy hv initiating the radical reaction from being absorbed by the solvent at the expense of the thioloester (I), it is important to choose the solvent so that it has a transparency greater than or equal to 50%, preferably to 70% and, still more preferably, to 90%, at the working wavelength.

Accordingly, in accordance with the invention the solvent is preferably selected from the following compounds: acetonitrile, ethanol, butanol, dichloromethane, cyclohexane, cyclopentane, 1,2dichloroethane, 2,2-dimethylbutane, n-heptane, n-hexane, methanol, 2-methylbutane, isooctane, n-pentane, 2-propanol, 1,2,2-trichlorotrifluoroethane, 2,2,2-trifluoroethanol or a mixture of these.

It is self-evident that the invention is not restricted to a method of activation by irradiation, especially by UV irradiation. Any other type of radical initiation can, in fact, be envisaged: heat, radical auxiliary (cf. above).

In accordance with an advantageous characteristic of the invention the solvent is chosen so that its boiling temperature at a given pressure is at least equal to, preferably substantially equal to, the reaction temperature $T_R$.

To obtain perhalo compounds which are in particular perfluoroalkylated and/or S-alkylated it is preferable to provide for a reaction temperature $T_R$ higher than or equal to 20° C. and, still more preferably, higher than or equal to 35° C. In practice $T_R$ may thus be of the order of, for example, 40° C.

On the other hand, when perhaloacylated, in particular perfluoroacylated, compounds are aimed at, $T_R$ is ideally lower than or equal to 30° C., preferably to 25° C. and, still more preferably, is of the order of 20° C.

Within the scope of the second route for implementing the process of the invention the substrate may be disulphide of the following formula:

$$R'—S—S—R'' \qquad (IV)$$

The radicals R' and R" in the compound (IV) and the radical R in the compound (I) may be identical or different from each other. They are preferably identical and correspond to the definition of R given above.

By way of examples of radicals R, R' and R" there may be mentioned —CH$_2$CH$_2$COOCH$_2$CH$_3$, phenyl, chlorophenyl, tert-butyl, n-butyl, cyclohexyl, benzyl, methyl, isopropyl, n-propyl, ethyl and octyl.

The preparation of thioesters CnF$_{(2n+1)}$SR (V) with the aid of a disulphide substrate (VI) benefits from a better yield than the direct conversion of the thioloester (I) to thioether (V) according to the first route of implementing the process according to the invention.

According to an alternative form of its second route of implementation, the process according to the invention consists in reacting a compound of formula (I) and especially the thioloester of formula (III) with an at least partially organic unsaturated substrate, preferably under irradiation at a wavelength included between 200 and 800 nm, at a reaction temperature $T_R$ and in an organic medium as defined above.

The result is a perhalo, preferably perfluoro, alkyl product in the case of $T_R$ 40–50° C. and a perhalo, preferably perfluoro, acyl product in the case of $T_R$ 20–30° C.

The olefinic substrates which can be envisaged for this perhaloalkylation or acylation and in particular for this trifluoromethylation (CF$_3$—) or trifluoroacetylation (CF$_3$—CO—) with the aid of thioloesters (I) of trifluoroacetic acid (CF$_3$COSR) are, especially, alkenes, cycloalkenes, (cyclo) alkynes, aromatics or mixtures of these.

The olefinic substrate is preferably characterized in that it is formed by at least one of the materials belonging to at least one of the following chemical classes:

alkenes and alkynes which are not functionalized on the unsaturation,
ethers and enol esters,
enol perhalocarboxylates,
vinyl sulphides,
enamines,
enoxy, enethio and enaminostannanes,
allystannanes,
enoxy, enethio and enaminosilanes,
allylsilanes.

With regard to the stoichiometry which is specific to the preferred embodiments of the process according to the invention (2nd route), it should be considered that the molar ratio of the compound of formula (I) to the substrate is advantageously between 0.1 and 10, preferably between 0.5 and 2 and, still more preferably, between 0.9 and 1.1.

When the reactant according to the invention is reacted with a carbon-carbon double bond, the resulting free radical can proceed in various ways and especially may combine with the sulphur-containing radicals of the media or else abstract a hydrogen from a compound carrying it. If it is desired to promote the hydrogen abstraction reaction (because it gives the addition of the perfluoroalkyl to one of the carbons and of a hydrogen to the other) it is appropriate to introduce into the reaction mixture products such as diphenylmethane, toluene, xylenes or even allyls, which are capable of donating a hydrogen atom to a free radical.

In accordance with the invention the compounds of formula (I) are novel agents for radical perhaloalkylation and/or -S-alkylation and/or acylation, the halogen considered being preferably fluorine. These thioloesters (I) have the advantage of being easy to prepare and to use, economical and ecologically tolerable.

It is no doubt superfluorous to observe that only those compounds according to the formula in which M is carbon give acylations.

The perhalo(fluoro)alkyl thioesters and the perhalo (fluoro)alkylated or acylated products obtained by the process according to the invention are notably capable of being exploited in the pharmaceutical or plant-protection sector.

However, one of the most innovative and most advantageous applications consists in making derivatives which are at the same time silanated and have at least one perfluorobranching.

These compounds, which are difficult to prepare, offer a great advantage. By employing the technique according to the present invention it is possible in particular to carry out such a synthesis either by perfluorination of a derivative which has a silane functional group and an unsaturation in a nonvinyl position or by perfluorinating a compound which has two double bonds and then silylating the remaining functional group.

Thus, according to the invention it is particularly advantageous to subject to the process according to the invention compounds of formula (V) below:

$(R_4)(R_5)C=C(R_6)(R_7)$ (V)

with $R_4$, $R_5$, $R_6$ and $R_7$, which are similar or different, chosen from hydrogen, hydrocarbon radicals and especially from alkyls, including cycloalkyls and aralkyls, and from aryls, with the condition that at least one of the $R_4$, $R_5$, $R_6$ and $R_7$ denotes:

- a monovalent radical carrying a silicon atom at a distance from the free valency of at least one, advantageously of at least two, carbon atoms;
- a monovalent radical carrying a nonaromatic double bond in a nonvinyl position with the free valency.

The radicals $R_4$ and $R_5$ may be joined to their corresponding radical (that is to say in a cis position) $R_6$ or $R_7$ to form one or two advantageously nonaromatic rings. It is preferable, however, that there should be only one ring thus formed.

The products thus formed are of formula VI:

$(R_4)(R_5)CH—C(Rf)(R_6)(R_7)$ (VI)

or $(R_4)(R_5)C(SR)—C(Rf)(R_6)(R_7)$ (VII)

in which $R_4$, $R_5$, $R_6$ and $R_7$ have the same value as in formula (V).

Rf advantageously has at least two, preferably at least four carbons. In addition, p+m is advantageously at least equal to two, preferably at least to four.

It is desirable that only one of $R_4$, $R_5$, $R_6$ and $R_7$ should carry a nonaromatic double bond or one (or more) silicon atoms(s).

As the perfluoroalkylation reaction is highly sensitive to steric hindrance of the substrate, it is preferable that among the radicals $R_4$, $R_5$, $R_6$ and $R_7$ there should be at least one, preferably at least two which denote hydrogen atoms.

It is preferable that among the radicals $R_4$, $R_5$, $R_6$ and $R_7$ there should be at most one which denotes a hindering radical. A hindering radical is intended in the present description to mean a radical in which the atom carrying free valency should additionally carry two and, above all, three branchings of at least one carbon.

Bearing the above in mind, it should be reported that the reaction is highly selective between the double bonds which are not highly hindered and those which are.

The invention will be understood better and its advantages and its alternative forms of embodiment will emerge properly from the examples which follow and which describe the preparation of thioethers and of perfluoroalkylated or acylated compounds with the aid of thioloesters (I) of a perfluorocarboxylic acid, which the said invention concerns.

EXAMPLES

EXAMPLE 1

Synthesis of the Thioloesters of Formula (I)

As far as the synthesis is concerned, generally speaking the thioloesters do not differ from the methods known to those skilled in the art for nonfluorinated thioloesters.

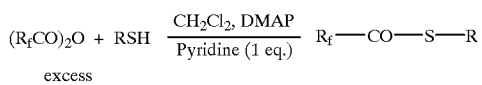

Derivatives of trifluoroacetic acid are used as a paradigm example for this reaction:

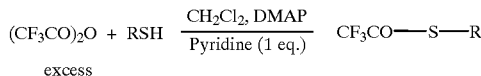

DAMP=4-dimethylaminopyridine 1.1 General Procedure 150 ml of dichloromethane (distilled and dried on 4-angstrom molecular sieve) are introduced into a 500-ml three-necked flask under a stream of nitrogen.

Pyridine (4 ml, 50 mmol), the thiol (50 mmol) and a spatula-tipful of DAMP are added next.

The reaction mixture is cooled to 0° C. with an ice bath and a solution of trifluoroacetic anhydride (8 ml, 57 mmol) in 50 ml of anhydrous $CH_2Cl_2$ is added dropwise.

The addition takes approximately 15 minutes.

The reaction is followed by vapour phase chromatography (VPC).

The reaction mixture is left at ambient temperature for 1 hour and in the case of a weakly nucleophilic thiol it may be heated to boiling for 1 additional hour.

The reaction mixture is poured into 150 ml of $H_2O$ and is extracted twice with $CH_2Cl_2$. The organic phase is dried over $MgSO_4$, filtered and concentrated in a rotary evaporator under water-pump vacuum without heating. The crude product obtained is distilled.

TABLE 1

| —R: | Isolated $CF_3COSR$ yield based on the thiol (%) | $Bp_p$ | | Mp |
|---|---|---|---|---|
| | | p = 20 | p = 760 | |
| —$CH_2CH_2CO_2Et$ | 95 | 101–102 | — | — |
| —Ph | 96 | 69–74 | — | — |
| -4-Cl—Ph— | 87 | 123–124 | — | — |
| -tert-butyl | 63 | — | 99 | — |
| -cyclohexyl | 80 | 94 | — | — |
| $PhCH_2$ | 84 | 115–117 | — | — |
| -Et | Commercial product | — | — | — |
| —$(CH_2)_7CH_3$ | 97.5 | 120 | — | — |
| $CH_2CO_2Et$ (*) | 81 | 90 | — | — |
| | 94 | — | — | 78 |
| —$CH_2CH(NH_3Cl)CO_2R^t$ (L) $R^t$ = Me $R^t$ = Et | 94 | — | — | 73 |

Abbreviations $Bp_p$=boiling temperature in ° C. at a pressure p in mm Hg,

Mp=melting point in ° C. at 760 mm Hg,

Et=ethyl, Ph=phenyl, 4-Cl-Ph=p-chlorophenyl, p=pressure in mm of mercury

=In the case of the L-cysteine esters the procedure is different:

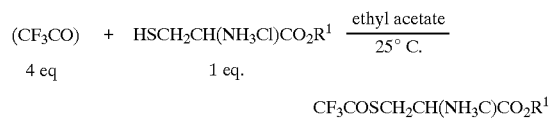

EXAMPLE 2

Preparation of Various Thio Ethers $CF_3$—S—R (III)

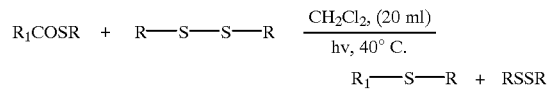

Derivatives of trifluoroacetic acid can be used as a paradigm example for this reaction.

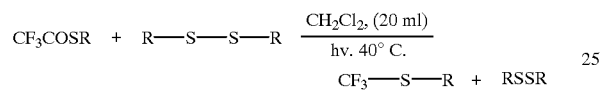

Into a quartz cell are introduced 20 ml (except in test 1:50 ml) of distilled and anhydrous dichloromethane (dried on 4-angstrom molecular sieve) which are deoxygenated with nitrogen for 15 minutes.

The thioloester and the disulphide are introduced next and are irradiated with a high-pressure mercury vapour UV lamp of HPK 125 type (power =125W) and of registered trademark Philips® (except for test 1: low-pressure HANOVIA® NK 12.

The reaction is followed by VPC.

A determination of the crude product at the end of radiation may be carried out by $^{19}F$ NMR (200 MHz) in the presence of (trifluoromethoxy)benzene as internal standard. The reaction mixture is then concentrated without heating under water-pump vacuum. The products are separated by chromatography on a silica column.

2.2 Results

Table II, attached to page 30, shows the reaction conditions and the data collected for various substituents R.

TABLE II

| R | Test numbers | $CF_3COSR$ (I) (mmol) | RSSR (II) (mmol) | Time | $CF_3SR$ (III) (mmol) | Unreacted $CF_3COSR$ (I) (mmol) | RSSR (II) recovered (mmol) | RY (%) | $DC^1$ (%) | $DC^2$ (%) |
|---|---|---|---|---|---|---|---|---|---|---|
| $CH_2CH_2$—CO—OEt | 1 | 2.5 | 2.3 | 4 h | 0.90 | 0 | 2.3 | 36 | 54 | 0 |
| | 2 | 1.88 (2 batches) | 0 | 2 × 1 h 15 | 0.60 (0.58) | 0.13 | 0.245 | 32 | 93 | — |
| | 3 | 1 | 0.95 | 1 h 45 | 0.64 (0.63) | (0.21) | 0.75 | 64 | 79 | 21 |
| | 4 | 0.97 | 0.36 | 1 h 15 | 0.48 | 0 | 0.36 | 49.5 | [90] | 0 |
| | 5 | 0.96 | 1.95 | 1 h 15 | 0.64 | 0 | 1.80 | 67 | ~80 | 8 |
| | 6 | 0.95 | 0.18 | 1 h 20 | 0.42 | 0 | 0.23 | 44 | 97 | — |
| ⟨⟩ | 7 | 2.01 (2 batches) | 0 | 2 × 1 h 15 | 0.35 (0.51) | [0.19] | 0.39 | 19.5 (25.5) | 90.5 | — |
| | 8 | 0.94 | 1.04 | 1 h 30 | 0.20 (0.28) | [0.16] | 1.05 | (30) | 72 | 0 |
| $C[(CH_3)]_3$ | 9 | 1.1 | 0 | 1 h | (0.22) | (0.042) | not det. | 20 | 96 | — |
| $(CH_2)_7CH_3$— | 10 | 2 × 0.95 | 0 | 2 × 1 h 15 | 0.72 (0.59) | (0.02) | 0.31 | 38 (31) | 99 | — |
| | 11 | 0.95 | 0.93 | 1 h 45 | 0.63 (0.68) | (0.08) | 0.93 | 66 (72) | 92 | 0 |
| —Φ | 12 | 1.1 | 0 | 1 h 30 | (0.16) | (0.19) | 0.42 | 14.5 | 83 | — |
| | 13 | 1.1 | 0.88 | 3 h 00 | 0.17 (0.29) | (0.25) | 0.50 | 26 | 77 | 43 |
| —ΦCl | 14 | 1.15 + 1.2 | 0 | 2 × 1 h 30 | 0.41 (0.42) | (0.35) | 0.53 | 17.5 | 85 | — |
| | 15 | 1.1 | 1.07 | 3 h 30 | 0.29 (0.31) | (0.39) | 1.29 | 27 | 75 | — |
| —$CH_2$—Φ | 16 | 1.09 + 1.1 | 0 | 1 h 30 | 0.16 (0.20) | (0.18) | [0.12] | 7.5 (9) | 92 | — |
| —$CH_2CO_2Et$ | 17 | 2.08 (2 batches) | 0 | 2 × 1 h 20 | 0.34 (0.58) | (0.106) | 0.17 | 16 (28) | (95) | — |
| | 18 | 0.97 | 1 | 2 h 05 | (0.445) | (0.12) | 0.84 | (46) | (87) | 16 |
| L-$CH_2CH(CO_2Me)$ | 19 | 0.86 | 0 | 2 h 15 | 0.27 (0.175) | 0 | 0.17 | 31 | 100 | — |
| ($NHCOCF_3$) | 20 | 1.00 | 1 | 1 h 50 | 0.60 | 0 | 1.09 | 60 | 100 | — |

TABLE III

| Test No. | (I) (mmol) | (II) (mmol) | Unreacted (I) (mmol) | (II) recovered at the end (mmol) | (III) (mmol) | (IV) (mmol) | RY of (III) (%) | CY of (I) (%) |
|---|---|---|---|---|---|---|---|---|
| 21 | 1.1 | 0.98 | (0.1) | 0.60 | 0.20 (0.34) | 0.45 | 18 (30.5) | 92 |

TABLE IV

| | | | | | CF$_3$COSR (I) | | (VI) | | (VII) | | (III) | |
|---|---|---|---|---|---|---|---|---|---|---|---|---|
| | x | y | | | Number of moles | | | | | | | |
| Test numbers | (mmol) (I) | (mmol) (V) | v (ml) | t (h) | which have not reacted | CY (%) | Number mmol | RY (%) | Number mmol | RY (%) | Number mmol | RY (%) |
| 22 | 0.98 | 5 | 20 | 1 h 45 | (0.25) [0.22] | 76 | (0.37) | 38 | (0.075) | 7.5 | (0.11) | 11 |
| 23 | 1 | 4.95 | 10 | 6 h 30 | (0.225) | 77.5 | (0.38) | 38 | (0.11) | 11 | (0.10) | 10 |
| 24 | 2 | 9.9 | s | 10 h 20 | (1.1) | 45 | (0.37) | 18.5 | (0.21) | 10.5 | (0.1S) | 7.5 |
| 25 | 1.2 | 1 | 20 | 1 h 45 | [0.38] (0.41) | 67 | (0.35) | 29* | (0.015) | 1* | (0.13) | 11 |
| 26 | 0.96 | 2.5 | 20 | 1 h 45 | [0.25] (0.28) | 72 | (0.27) | 28 | (0.04) | 4 | (0.10) | 10.5 |
| 27 | 1 | 0.4 | 20 | 0 h 45 | [0.40] (0.53) | 47 | 0.22 | 55* | 0 | 0 | (0.11) | 11 |
| 28 | 0.95 | 4.95 | 20 | 1 h 45 | — | 73 | — | 24 | — | 18 | — | 12.5 |
| 29 | 1.4 | 1 | 10 | 2 h 00 | 0.72 | 49 | 0.38 | 38* | — | — | 0.17 | 12 |
| 30 | 1 | 5 | 10 | 6 h 35 | — | (75) | — | (28) | — | (10) | — | (8.5) |
| 31 | 1 | 5 | 10 | 4 h 00 | — | (87) | — | (34) | — | (13) | — | (9.5) |
| 32 | 1 | 5 | 20** | 1 h 30 | — | (63) | — | (11) | — | (14) | — | (3.3) |

\* = vs cyclohexene
\*\* solvent = chlorobenzene

RY=yield of compound obtained, based on the reactant (I) or substrate (II) introduced:
DC$^1$=degree of conversion of reactant (I) equal to:
DC$^2$=degree of conversion of reactant (II) equal to:
CY=yield of compound obtained, based on the reactant (I) or substrate (II) consumed:
In this table II the results in brackets are obtained by $^{19}$F NMR determination with an internal standard.

EXAMPLE 3

Preparation of Various Thioethers CF$_3$—S—R$^3$ 2.1 General Procedure

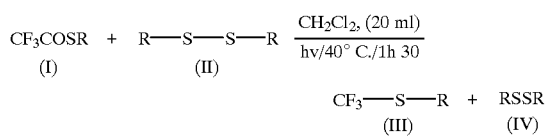

with:
R=t—Bu,
R$^1$=R$^2$=CH$_2$CH$_2$CO$_2$Et,
R$^3$=R$^1$=R$^2$=CH$_2$CH$_2$CO$_2$Et.

The methodology is identical with that in Example 2.
Table III, shows the results obtained as a function of the reaction conditions.

EXAMPLE 4

Perfluoroalkylation and Perfluoroacylation of Cyclohexene with the Aid of a Reactant of Formula (I): CF$_3$COSR

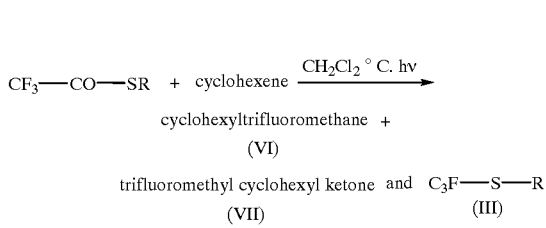

The UV irradiation is performed with the aid of the same lamp as in Examples 2 and 3.

In a first series of tests (tests 22 to 28), the substituent R in (I)=—CH$_2$CH$_2$CO$_2$Et with the reaction temperature of 40° C. in the case of tests 22 to 27 and of 20° C. in the case of test 28.

The second series includes the tests 29 and 30 carried out at T$_R$=40° C. in the case of R=—CH$_2$CH$_3$.

The third series of tests (31 and 32) corresponds to a substituent R=Ph, with T$_R$=40° C. in the case of test 31 and T$_R$=20° C. in the case of test 32.

Table IV, appended to page 32, shows the test conditions and the results.

In this Table IV, the results identified by round brackets "()" have been obtained by determination using $^{19}$F NMR (with internal standard) and those identified by square brackets "[]" by VPC determination (with internal standard).

EXAMPLE 5

Perfluoroalkylation of Olefins 5.1 7-Tetradecene (VIII):

The operating method and conditions are given below. In a first step this involves the perfluoroalkylation (CF) Example 4):

$$CF_3\text{-}COSEt + CH_2\!=\!CH\text{---}(CH_2)_3\text{---}CH_3 \xrightarrow{CH2Cl2\ h\nu}$$

•$CF_3(CH_2)_{11}CH_3$
(XII)

$CF_3CH_2\text{•}CH(CH_2)_9CH_3$ (XIII)

•$CF_3SEt$ (III)

$CF_3CH\!=\!CH\text{•}(CH_2)_9CH_3$  •$CF_3CH_2\text{---}CH\!=\!CH\text{•}(CH_2)_8CH_3$ operating conditions:
time 3 hours
temperature: at 40° C.
activation by irradiation in methylene chloride in the above conditions.

The results obtained by $^{19}F$ NMR determination are given in Table V below.

5.2.2. Reduction:

In a second step a reduction is used to permit the hydrogenation of olefins [$H_2$/Pd/C(10%)/2 bar (=)$2\times10^5$ pascals in acetic acid]:

$RY_{overall}=46\%$ based on the olefin (XI).

EXAMPLE 6

Synthesis of Perfluoroalkylated Alcohols by Perfluoroalkylation of Enol Acetates An enol acetate is irradiated in the presence of $CF_3COSEt$ (I) using the conditions of Example 4. After evaporation of methylene chloride the resulting mixture of trifluoro-methyl compounds is taken up in ethyl ether and treated with lithium aluminium hydride at 20° C.:

$$CF_3\text{---}COSEt + \underset{XIV}{\overset{AcO\quad H}{\underset{R_4\text{---}CH_2\quad R_3}{\diagup\!\!\!\diagdown}}} \longrightarrow$$

TABLE V

| Test No. | $CF_3COSEt$ (mmol) (I) | Olefin (mmol) (VIII) | Remaining $CF_3COSEt$ (I) mmol | CY (%) | Remaining olefin (VIII) mmol | CY (%) | (IX) nb mmol | CY (%) | nb mmol | RY (%) | nb mmol | RY (%) |
|---|---|---|---|---|---|---|---|---|---|---|---|---|
| 33 | 1.8 | 1.1 | (0.45) | 75 | 0 | 100 | (0.43) | 39 | (0.04) | 3.5 | (0.4) | 22 |

In a second step a reduction (hydrogenation) is carried out to permit the conversion of (X) to (IX). Conditions employed: $H_2$/Pd/C (10%)/2 bar ($2\times10^3$ pascals):
$RY_{overall}=41\%$ based on the olefin (VIII).

5.2 1-Dodecene (XI):
5.2.1 Perfluoroalkylation (cf. Example 4):
operating conditions
time 3½ hours
temperature: at 40° C.
activation by irradiation in methylene chloride in the above conditions.
RESULTS:

-continued $$\underset{XV}{\overset{AcO\ CF_3\ H}{\underset{R_4\text{---}CH_2\quad R_3}{\diagup\!\!\!\diagdown}}} + \underset{XVI}{\overset{AcO\ CF_3\ H}{\underset{R_4\text{---}CH_2\quad R_3}{\diagup\!\!\!\diagdown}}} + \underset{III}{CF_3\text{---}COSEt}$$

$$\underset{XV}{\overset{AcO\ CF_3\ H}{\underset{R_4\text{---}CH_2\quad R_3}{\diagup\!\!\!\diagdown}}} +$$

TABLE VI

| Test No. | $CF_3COSEt$ (mmol) (I) | Olefin (mmol) (VIII) | Remaining $CF_3COSEt$ (I) mmol | CY (%) | Remaining olefin mmol | CY (%) | (XII) nb mmol | CY (%) | (XIII) nb mmol | RY (%) | (III) nb mmol | RY (%) |
|---|---|---|---|---|---|---|---|---|---|---|---|---|
| 34 | 1.56 | 0.96 | 0.62 | 60 | 0 | 100 | (0.34) | 35.5 | (0.07) | 7.5 | (0.325) | 21 |

COMMENTARIES:
110 mg of a mixture containing the following, in proportion by $^{19}F$ NMR, are isolated:
85.5% of $CF_3(CH_2)_{11}CH_3$,
14.5% of $CF_3CH\!=\!CH\text{---}(CH_2)_9CH_3$ and $CF_3CH_2\text{---}CH\!=\!CH(CH_2)_8CH_3$.

-continued

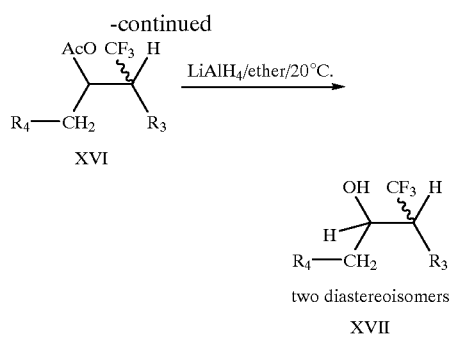

two diastereoisomers
XVII

EXAMPLE 7

Preparation of CF₃—S—Ph by Thermolysis of CF₃CO—S—Ph

A spiral Pyrex tube 2 m in length and 4 mm in diameter is heated for 4 hours to 600° C. under argon atmosphere in a cylindrical oven. It is then placed, successively, at the different temperatures shown in Table VIII below. In each experiment 0.5 g of S-phenyl trifluorothioacetate (I) is introduced into an injector connected to this oven. This compound is heated to boiling and passes through the tube at autogenic pressure. The products are recovered in an ice-cooled flask. The loss in weight is small. The mixture of fluoro compounds contains trifluoromethyl phenyl sulphide (III) and starting material (I). Table VII, which follows, shows the proportions as a function of the temperature.

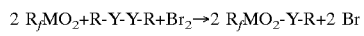

1 equivalent of disulphide (diselenide) is added to a flask containing 2 equivalents of triflinate in suspension in $CH_2Cl_2$ and then 1 equivalent of bromine in 1M solution in $CH_2Cl_2$ is run in.

8 h 00 min later (VPC monitoring) the reaction mixture is filtered, the solvent is evaporated off and the compound is purified by distillation or recrystallization from petroleum ether.

2nd method

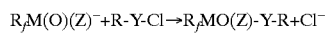

1 equivalent of sulphenyl (selenenyl) chloride in solution in $CH_2Cl_2$ is poured into a flask containing 1 equivalent of triflinate in suspension in $CH_2Cl_2$. The reaction is relatively fast.

The reaction mixture is filtered and the solvent evaporated off; the compound is clean.

| Compound | Method of synthesis | Yield | ¹⁹F NMR (CDCl₃ relative to CFCl₃) | Melting pt. |
|---|---|---|---|---|
| $CF_3SO_2SCH_2CO_2Et$ | 1 | 88% | −78.95 | — |
| $CF_3SO_2SCO_2Me$ | 2 | 96% (¹⁹F NMR determi- | −75.91 | — |

TABLE VII

RESULTS

| | | | (I) recovered | | Olefin recovered (XIV) | | (XVI) | | (XV) | | (III) | | (XVII) | | |
|---|---|---|---|---|---|---|---|---|---|---|---|---|---|---|---|
| R⁴ | R⁵ | x mmol | y mmol | t h | mmol | DC¹ % | mmol | DC² % | mmol RY % | mmol | RY % | mmol | RY % | mmol | mmol | RY % |
| R⁴-R⁵ = (CH₃)₃ | | 1.4 | 0.99 | 2 h 05 | (0.34) | (76) | 0 | 100 | (0.26) | (26) | (0.05) | (3) | (0.325) | (23) | 0.9 | 0.3 | 30 |
| n— | n— | 2 × 1.4 | 0.99 + 0.90 | 2 × 2 h 05 | 0.40 | 86 | 0.55 | 71 | — | — | — | — | 0.73 | 26 | 7.5 | 0.4 | 21 |
| C₄H₉ | C₄H₉ | 3 × 0.7 | 3 × 0.455 | 3 × 3 h | — | — | 0 | 100 | — | — | — | — | — | — | 4 | 0.42 | 31 |

RESULTS:

TABLE VIII

| T(° C.) | (I) (%) | (III) (%) |
|---|---|---|
| 400 | 98 | 2 |
| 450 | 95 | 5 |
| 500 | 80 | 20 |
| 550 | 75 | 25 |

EXAMPLE 8

Synthesis of Derivatives of Formula $R_f\text{-M(X)(Z)}_n\text{-Y-R}$ when M is a Chalocogen (M=S, Se) Using $CF_3SO_2YR$ (Y=S, Se) as Paradigm of the Class Synthesis of $CF_3SO_2YR$ (Y=S, Se)

1st method $$2\ R_fMO_2 + R\text{-Y-Y-R} + Br_2 \rightarrow 2\ R_fMO_2\text{-Y-R} + 2\ Br$$

$$R_fM(O)(Z)^- + R\text{-Y-Cl} \rightarrow R_fMO(Z)\text{-Y-R} + Cl^-$$

-continued

| Compound | Method of synthesis | Yield | ¹⁹F NMR (CDCl₃ relative to CFCl₃) | Melting pt. |
|---|---|---|---|---|
| | | nation) | | |
| $CF_3SO_2S(CH_2)_7CH_3$ | 1 | 88% | −78.96 | — |
| $CF_3SO_2S\text{-tBu}$ | 1 | 0% | — | — |
| $CF_3SO_2S\text{-cyclohexyl}$ | 1 | 65% | −79.25 | — |
| $CF_3SO_2S\text{-}\Phi$ | 1 | 50%–67% | −75.8 | 38–39° C. |
| | 2 | 84% | | |
| $CF_3SO_2S\text{-}\Phi\text{-NO}_2$ | 2 | 93% | −75.32 | 76–77° C. |
| $CF_3SO_2S\text{-}\Phi\text{-Cl}$ | 2 | 50% | −75.46 | — |
| $CF_3SO_2S\text{-CH}_2\text{-}\Phi$ | 1 | 90% | −78.64 | — |
| $CF_3SO_2S\text{-CCl}_3$ | 2 | 95% | −75.2 | — |
| $CF_3SO_2Se\text{-}\Phi$ | 2 | 95% | −77.6 | not |

-continued

| Compound | Method of synthesis | Yield | $^{19}$F NMR (CDCl$_3$ relative to CFCl$_3$) | Melting pt. |
|---|---|---|---|---|
| | | unstable product | | determinable because solid degrades thermally |

Synthesis of CF$_3$SR by photolysis

1 mmol of CF$_3$SO$_2$SR is introduced into 20 ml of anhydrous CH$_2$Cl$_2$ in a 20-ml quartz cell. 1 mmol of corresponding disulphide is introduced next. The reaction mixture is degassed for 10 minutes with dry nitrogen and is then irradiated for 40 minutes at 40° C. (solvent reflux) with a Phillips HPK 125 UV lamp (125 W, mercury vapour, high pressure).

The expected product is then purified by flash chromatography. The starting disulphide is recovered virtually completely.

CF$_3$SeR 1 equivalent of corresponding selenenyl chloride is poured into a flask containing 1 equivalent of triflinate in suspension in CH$_2$Cl$_2$ and 2 equivalents of diselenide.

At the end of the addition the reaction mixture is heated to 40° C. for 24 h.

The expected produce is purified by flash chromatography. The starting diselenide is recovered virtually completely.

This compound can also be obtained without employing selenenyl chloride. Following the same procedure as previously but with 3 equivalents of starting diselenide, 1 equivalent of Br$_2$ in 1M solution in CH$_2$Cl$_2$ is then poured in instead of the selenenyl chloride.

| Compound | Yield $^{19}$F NMR determination | Isolated | $^{19}$F NMR (CDCl$_3$ relative to CFCl$_3$) |
|---|---|---|---|
| CF$_3$S-Φ | 25% | 20% | −43.37 |
| CF$_3$S(CH$_2$)$_7$CH$_3$ | 80% | 74% | −41.58 |
| CF$_3$SCH$_2$CH$_2$CO$_2$Et | 78% | 65% | −41.87 |
| CF$_3$Se Method with RSeCl | 90% | 74% | |
| CF$_3$Se Method with Br$_2$ | 80% | 70% | −36.6 |

EXAMPLE 9

Photochemical Grafting Onto Olefins 1 mmol of CF$_3$SO$_2$SR is introduced into 20 ml of anhydrous CH$_2$Cl$_2$ in a 20-ml quartz cell. 1 mmol of alkene is introduced. The reaction mixture is degassed for 10 minutes with dry nitrogen and is then irradiated for 1 h 15 min with a Phillips HPK 125 lamp (125 W, mercury vapour, high pressure).

The products are determined by $^{19}$F NMR and identified by gas chromatography/mass spectrometry in tandem.

| ALKENE | Number of equivalents of CF$_3$SO$_2$SΦ | Yield (by determination) | Product |
|---|---|---|---|
| CH$_2$=CH—(CH$_2$)$_8$—CH$_3$ | 1 | 36% | CF$_3$—(CH$_2$)$_{10}$—CH$_3$ |
| | | 12% | CF$_3$CH=CH—(CH$_2$)$_8$—CH$_3$ or CF$_3$—CH$_2$—CH=CH—(CH$_2$)$_8$—H |
| | | 11% | CF$_3$—CH—CH(SΦ)—(CH$_2$)$_9$—H |
| CH$_2$=CH—(CH$_2$)$_8$—CH$_3$ | 2 | 33% | CF$_3$—(CH$_2$)$_{10}$—CH$_3$ |
| | | 49% | CF$_3$—CH—CH(SΦ)—(CH$_2$)$_9$—H |
| CH$_2$=CH(CH$_2$)$_8$—CH$_3$ | 3 | 30% | CF$_3$—(CH$_2$)$_{10}$—CH$_3$ |
| | | 46% | CF$_3$—CH—CH(SΦ)—(CH$_2$)$_9$—H |
| CH$_2$=CH—C(CH$_3$)$_2$—CH$_2$—COOMe | 2 | 45% | CF$_3$—CH$_2$—CH$_2$—C(CH$_3$)$_2$—CH$_2$COOMe |
| | | 45% | CF$_3$—CH—CH(SΦ)—C(CH$_3$)$_2$—CH$_2$—COOMe |
| CYCLOHEXENE | 1 | 26% 13%/traces | CYCLOHEXYL —CF$_3$ 1-trifluoromethyl 2-thiophenyl cyclohexane (2 diastereoisomers) |
| CYCLOHEXENE | 2 | 25% 30%/10% | CYCLOHEXYL —CF$_3$ 1-trifluoromethyl 2-thiophenyl cyclohexane (2 diastereoisomers) |

EXAMPLE 10

Synthesis of Octyl Pentadecafluorothiooctanoate
C$_7$F$_{15}$COS(CH$_2$)$_7$CH$_3$ 12 ml of anhydrous dichloromethane, 0.86 ml (5 mmol) of n-octanethiol and 0.90 g (7.5 mmol) of dimethylaminopyridine are introduced into a 50-ml three-necked flask fitted with a thermometer, a magnetic stirrer and supporting a reflux condenser. The reaction mixture is cooled to 0° C. with the aid of an ice bath. A solution of pentadecafluorothiooctanoyl chloride (1.6 ml, 6.5 mmol) in 10 ml of anhydrous dichloromethane is then added dropwise over 20 minutes.

At the end of addition the temperature of the reaction mixture is allowed to rise again and the latter is kept at ambient temperature for 2 h 30 min and is then heated to reflux for 1 h. 0.135 ml (2.5 mmol) of trifluoroacetic acid is then added. The product is purified by flash chromatography on silica (10 g) with dichloromethane as eluent. Phases of identical nature (VPC) are combined and dried over magnesium sulphate. The solvent is removed by evaporation under water pump vacuum at ambient temperature. 2.29 g of a colourless liquid with a nauseating odour are obtained (yld 90%).

$^1$H NMR (200, 13 MHz, CDCl$_3$)
S (ppm)=0.9 (m, 3H, CH$_3$); 1.3 (m, 10H); 1.6 (m, 2H, SCH$_2$CH$_2$); 3.1 (t,J=7.3 H$_z$, 2H, SCH$_2$).
$^{19}$F NMR (188.35, MHz, CDCl$_3$) CF$_3$—CF$_2{}^f$—CF$_2{}^e$—CF$_2{}^d$—CF$_2{}^c$—CF$_2{}^b$—CF$_2{}^a$COSC$_8$M$_{17}$
S(ppm)=−81.52 (t, $^h$J=9.5 H$_z$, 3F, CF$_3$); −116.29 (t, $^h$J=13.2 H$_z$, 2F, CF$_2{}^1$)
−121.91 (broad peak, 2F, CF$_2{}^b$), −122.42 (broad peak, 4F, CF$_2{}^c$, CF$_2{}^d$);
−123.20 (broad peak, 2F, CF$_2{}^a$), −126.69 (broad peak, 2F, CF$_2{}^f$).
$^{13}$C NMR (50.32 MHz, CDCl$_3$)
S(ppm)=13.78 (CH$_3$), 22.63 to 31.81 (7 CH$_2$), 108.96 to 120.79 (unresolved bands, CF$_n$); −186.52 (CO).

EXAMPLE 11

Synthesis of Methyl Pentadecafluorothiooctanoate C$_7$F$_{15}$COSCH$_3$

Methylene chloride (5 ml) and then CH$_3$SNa (0.14 g, 2 mmol) are introduced into a 50-ml three-necked flask fitted with a septum, a thermometer, a magnetic stirrer and supporting a reflux condenser. The reaction mixture is cooled with the aid of an ice bath and is kept under nitrogen atmosphere, and a solution of C$_7$F$_{15}$COCl (0.24 ml, 1 mmol) in 5 ml of dichloromethane is run in dropwise over 10 minutes. The temperature is allowed to return to the ambient over 1 h. The mixture is then heated under dichloromethane reflux for 2 h and then 0.1 ml (1 mmol) of trifluoroacetic acid is added. The reaction mixture is filtered on silica (10 g). The filtrate is dried over magnesium sulphate and then, after filtration on paper, the solvent is evaporated off under vacuum at ambient temperature. 0.38 g of a colourless liquid is obtained, i.e. a yield of 86%.

$^1$H NMR (200, 13 MHz, CDCl$_3$)
S (ppm)=2.49 (s, 3M, SCH$_3$)
$^{19}$F NMR: (188.35 MHz, CDCl$_3$) CF$_3$—CF$_2{}^f$—CF$_2{}^e$—CF$_2{}^d$—CF$_2{}^c$—CF$_2{}^b$—CF$_2{}^a$—COSCH$_3$
S(ppm)=−81.43 (t, $^h$J=9.9 H$_z$, 3F, CF$_3$), −116.97 (t, $^h$J=13.2 H$_z$, 2F, CF$_2{}^a$),
−121.87 (broad peak, 2F, CF$_2{}^b$), −122.51 (broad peak, 4F, CF$_2{}^{c,d}$),
−123.22 (broad peak, 2F, CF$_2{}^e$), −126.67 (broad peak, 2F, CF$_2{}^f$).
$^{13}$C NMR (50.32 MHz, CDCl$_3$)
S(ppm)=11.86 (CH$_3$), 107.67 to 120.96 (unresolved bands, CF$_n$), 187.13 (CO).
Mass spectrum (m/z, %)
m/z=444 (M,2), 397 (C$_7$F$_{15}$CO, 10), 75 (COSCH$_3$, 100), 69 (CF$_3$, 31), M7 (SCH$_3$, 45).

EXAMPLE 12

Grafting of R$_f$ onto Unsaturated Silanes
General procedure 20 ml of anhydrous dichloromethane and the reactant (thioesters, substrate) are introduced into a 50-ml cylindrical cell which has 2 plane faces made of quartz and is fitted with a magnetic stirrer. Nitrogen is bubbled through for 15 minutes. The reaction mixture is then subjected to ultraviolet irradiation at 40° C.

The progress of the reaction is followed by VPC. At the end of irradiation an internal standard (trifluoromethoxybenzene) is added and a $^{19}$F NMR analysis is performed to quantify the various fluorinated species.

The dichloromethane is then evaporated off under water pump vacuum without heating.

Case of octyl trifluorothiaacetate on the unsaturated cyclic silane

A solution consisting of CF$_3$COSC$_8$H$_{17}$ (0.2 kg, 1 mmol) and of unsaturated cyclic silane cyclohexenylethyl—Si(CH$_3$)(O—Et)$_2$ (0.24 g, 1 mmol) in 20 ml of anhydrous dichloromethane is irradiated for 2 h 20 min at 40° C. with stirring.

A crude mass of 0.480 g is obtained from which no product has been isolated because of the difficulty of separation of the disulphide from the other products.

A trifluoromethylation at 3 and at 4 positions is obtained with two diastereoisomers in each position.

$^{19}$F NMR (determination, 138.35 MHz, CDCl$_3$)
δ(ppm)=−41.75 (s, 3F, CF$_3$S), CF$_3$S(CH$_2$)+CH$_3$, yld=10%
−72.67 (broad s, 3F)
−74.28 (d, 'J=6.6 H$_z$, CF$_3$), yld=20+61%
−74.42 (d, 'J=6.7 H$_z$, CF$_3$)
−75.92 (s, 3F, CF$_3$CO) CF$_3$COSC$_8$H$_{17}$, conversion=96%
Mass spectrum (m/z, %)
rt=11.967 min (SCAN 309) (product 9)
m/z=153 (C$_5$H$_{14}$O$_2$SiF, 35), 133 (C$_5$H$_{13}$SiO, 100), 109 (C$_3$H$_{10}$SiOF, 13), 89 (C$_3$H$_9$SiO, 15), 61 (CH$_5$SiO, 10).
rt=12.127 min (SCAN 314) (product 9)
m/z=153 (C$_5$H$_{14}$O$_2$SiF, 37), 133 (C$_5$H$_{13}$SiO, 100); 109 (C$_3$H$_{10}$SiOF, 13); 89 (C$_3$H$_9$SiO, 12); 61 (CH$_5$SiO, 10).

EXAMPLE 13

Case of Methyl Pentadecaluorothioocanoate on the Unsaturated Cyclic Silane

The solution of C$_7$F$_{15}$COSCH$_3$ (0.44 g, 1 mmol) and of silane (0.24 g, 1 mmol) in 20 ml of anhydrous dichloromethane is irradiated under the same conditions for 5 h at 40° C. without stirring. The products degrade partially on silica. No purification was obtained.
VPC This analysis shows the formation of 4 isomeric (according to MS) products grouped as 2 pairs of products.
rt=0.61 min; 10.22%; C$_7$F$_{15}$SCH$_3$
rt=7.68 min; 55%
rt=7.81 min; 1.5% 4 isomeric products
rt=8.04 min; 22.7%
rt=8.17 min; 9.3%
$^{19}$F NMR (128.35 MHz, CDCl$_3$)
Determination with PhOCF$_3$ as standard:
C$_7$F$_{15}$SCH$_3$: 9.8%

$C_7F_{15}COSCH_3$: 5.7% crude yield for the sum of the h isomers=68.5%
Σ ($R_fCH$): 84%
Mass spectrum (m/z %)
Retention times of the isomers (in min): 1 h 55, 2 h 13, 15.15, 15.41.
Peaks common to the 4 isomers:
m/z=460 ($C_{15}HF_{14}$, 1); 432 ($C_{13}H_{10}F_{14}$, 1); 419 ($C_{12}H_8F_{14}$, 1); 153 ($C_5H_{14}O_2SiF$, 18); 133 ($C_5H_{13}SiO$, 100); 109 ($C_3H_{10}SiOF$, 11); 89 ($C_3H_9SiO$, 12); 61 ($CH_5SiO$, 4).

EXAMPLE 14

Grafting of $R_f$ onto a Diene

Case of ethyl trifluorothioacetate on 4-vinyl-cyclohexene

A solution of $CF_3COSH_2CH_3$ (0.16 g, 1 mmol) and of 4-vinylcyclohexene (1.10 g, 1 mmol) in 20 ml of anhydrous dichloromethane is irradiated for 5 h 20 min at 40° C. without stirring.
Determination by $^{19}F$ NMR (188.35 MHz, $CDCl_3$)
S(ppm)=−64.25 (m), 18(I), yld 6.9%
  −66.71 ($t^3$, J=10.9 Hz), 20(**), yld 30%
  −72.15 (m), 17 (?), yld 4.2%
  −72.80 (d, intensity $I^1$)
  19(***), yld 1.6%
  −72.98 (d, intensity $I^1$)
  −74.1 (d, intensity $I^2$)
  19(***), yld 4.2%
  −74.26 (d, intensity $I^2/2$)
(*) by analogy with S=−74.7 ppm for trans $CF_3CH=CHC_5H_{11}$
(C. J. Bicokes, P. L. Coe, A. E. Pedder, J. C. Tatlow, J. Chem. Soc., Perkin Trans. I, 1978, 202).

In $^{19}F$ NMR the ratio of trifluoromethylation between the exo double bond and the endocyclic double bond is roughly estimated at 3/1.

In $^1H$ NMR the ratio between the exo vinyl protons and the endocyclic vinyl protons is of the order of 2.3 and the ratio between the $CH_2CF_3$ and $CHCF_3$ units is in the region of 2.

One drop of product analysed by $^1H^{19}F$ NMR is obtained by microdistillation. The spectra are analogous with those of the crude product but the very high dilution of the sample does not allow the analysis to be refined.

An attempt was also made to chromatograph the product (silica mass=6 g, quantity of product introduced 130 mg) by eluting with petroleum ether. The conditions appear to be suitable for the separation of the mixture; nevertheless the very small quantity of product recovered in each fraction does not permit proper identification.

EXAMPLE 15

Synthesis of Pentadecafluoroheptyl Octyl Thioether $C_7F_{15}SC_8H_{17}$ a) In the absence of disulphide
A solution of $C_7F_{15}COSC_8H_{17}$ (0.55 g, 1 mmol) in 20 ml of anhydrous dichloromethane is irradiated for 3 h 20 min at 40° C. without stirring.

$^{19}F$ NMR (188.35 MHz, $CDCl_3$)
S (ppm)=−87.69 (t, $^4J$=12.5 Hz, 2F, $SCF_2$) yld=24 % →$C_7F_{15}SC_8H_{17}$
  −116.78 (t, 4J=13.2 Hz, 2F, $CF_2COS$) conversion= 67%→$C_7F_{15}COSC_8H_{17}$
  −137.8 (d, $^2J$=49.8 Hz, 2F, $CF_2H$) yld=28% →$C_6F_{13}$—$CF_2H$ b) In the presence of disulphide
A solution of $C_7F_{15}COSC_8H_{17}$ (0.55 g, 1 mmol) and of $C_8H_{17}S$ (0.3 g, 1 mmol) in 20 ml of anhydrous dichloromethane is irradiated for 3 h 15 min at 40° C. without stirring.

$^{19}F$ NMR (188.35 MHz, $CDCl_3$)
S(ppm)=−87.74 (t, $^4J$=12 Hz, 2F, $SCF_2$) yld=51% →$C_7F_{15}SC_8H_{17}$
  −116.98 (t, $^4J$=13.2 Hz, 2F, $CF_2CO$ (conversion= 80%→$C_7F_{15}CISC_8H_{17}$
  −137.4 (t, $^2J$=49.8 Hz, 2F, $CF_2H$) yld=20% →$C_6F_{13}$—$CF_2H$ After optimization of this reaction in respect of the irradiation period, a crude yield of 57% of $C_7F_{15}SC_8H_{17}$ with disappearance of the $C_6F_{13}CF_2H$ is obtained at 5 h 45 min at 40° C. without stirring.

$^{19}F$ NMR of $C_7F_{15}SC_8H_{17}$
$CF_3CF_2{}^fCF_2{}^eCF_2{}^dCF_2{}^cCF_2{}^bCF_2{}^aSC_8H_{17}$
S(ppm)=−81.09 (t, $^hJ$=9 Hz, 3F, $CF_3$), −87.68 (t, $^hJ$=12 Hz, 2F, $SCF_2$), −120.8 (broad peak, 2F, $CF_2{}^b$), −121.46 (broad peak, 2F, $CF_2{}^c$), −122.22 (broad peak, 2F, $CF_2{}^d$), −122.96 (broad peak, 2F, $CF_2{}^e$), −126.37 (broad peak, 2F, $CF_2{}^f$).

EXAMPLE 16

Synthesis of Pentadecafluoroheptyl Methyl Thioether $C_7F_{15}SCH_3$ a) In the absence of disulphide
A solution of $C_7F_{15}COSCH_3$ (0.44 g, 1 mmol) in 20 ml of anhydrous dichloromethane is irradiated for 4 h 37 min at 40° C. without stirring.

$^{19}F$ NMR determination of the crude mixture (128.35 MHz, $CDCl_3$)
S(ppm)=−91.18 (t, $^4J$=13.5 Hz, 2F, $SCF_2$) yld=53% (absence of $CF_2CO$ and of $CF_24$)

A few drops of a light-yellow liquid pure in $^1H$ and $^{19}F$ NMR are obtained by microdistillation at atmospheric pressure.

$^{19}F$ NMR (188.35 MHz, $CDCl_3$)
$CF_3CF_2{}^fCF_2{}^eCF_2{}^dCF_2{}^cCF_2{}^bCF_2{}^1SCH_3$
S(ppm)=−81.29 (t, $^4J$=8.5 Hz, 3F, $CF_3$), −90.92 (t, $^hJ$=14 Hz, 2F, $SCF_2$), −120.35 (broad peak, 2F, $CF_2{}^b$), −122.05 (broad peak, 2F, $CF_2{}^c$), −122.73 (broad peak, 2F, $CF_2{}^d$), −123.46 (broad peak, 2F, $CF_2{}^e$), −126.87 (broad peak, 2F, $CF_2{}^f$).
$^1H$ NMR (200.13 MHz, $CDCl_3$)
S(ppm)=2.4 (s, 3Y, $SCH_3$)

a) In the presence of disulphide
A solution of $C_7F_{15}COSCH_3$ (0.4 g, 1 mmol) and of disulphide ($CH_3S$—$S$—$CH_3$) (0.09 g, 1 mmol) in 20 ml of anhydrous dichloromethane is irradiated at 40° C. with stirring for 4 h 50 min.

$^{19}F$ NMR determination of the crude mixture (188.35 MHz, $CDCl_3$)
S(ppm)=−90.67 (t, $^hJ$=13.2 Hz, 2F, $SCF_2$) yld=81%
  −116.79 (t, $^hJ$=9 Hz, 2F, $CF_2CO$) conversion= 95%→$C_7F_{15}COSCH_3$ After evaporation of the solvent the residue is purified by flash chromatography on silica (10 g) starting with 0.332 g of product The eluent employed is petroleum ether. After evaporation of the fractions at 60–70° at atmospheric pressure, 0.110 g of $C_7F_{15}SCH_3$ which is pure in $^1H$ and $^{19}F$ NMR is isolated, representing a yield of 40%. The use of pentane as eluent will probably make it possible to obtain a higher yield of isolated product.

EXAMPLE 17

Photolysis of the Thioloester

S-Trifluoroacetyl ethylxanthate was photolysed in bulk, without solvent:

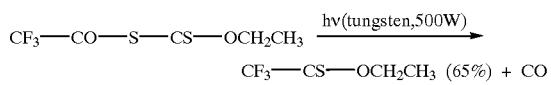

An attempt was made to photolyse this thioloester in the conditions developed previously, that is to say in solution in dichloromethane:

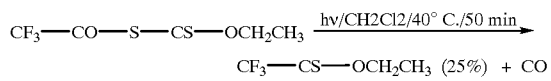

EXAMPLE 18

Photolysis of S-trifluoroacetyl Ethylxanthate in the Presence of 1-dodecene

Test in solution

A solution of S-trifluoroacetyl ethylxanthate (0.22 g, 1 mmol) and of 1-dodecene (0.17 g, 1 mmol) in 20 ml of anhydrous dichloromethane, contained in a cylindrical reactor made of Pyrex glass of identical characteristics to that made of quartz, is irradiated at 40° C. (HPK 125 lamp):

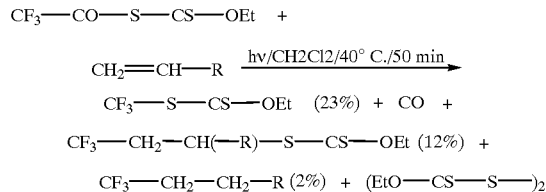

In solution, the formal cis-addition of $CF_3$—SC(S)OEt to 1-dodecene remains in the minority (12%) but the hydrotrifluoromethylation of this olefin is reduced to only 2%.

The thioloester considered is therefore indeed cleaved photochemically and the decarbonylation of the trifluoroacetyl radial generated does result, here too, in the trifluoromethyl radical. However, only approximately 40% of the $CF_3$ unit introduced is found again, predominantly in the product of formal decarbonylation of the initial radical (RY=23%). The major proportion of the trifluoromethyl radical is in the form of gaseous compounds like $C_2F_6$ $CF_3H$ or $CF_3Cl$.

Test in the absence of solvent and in two steps

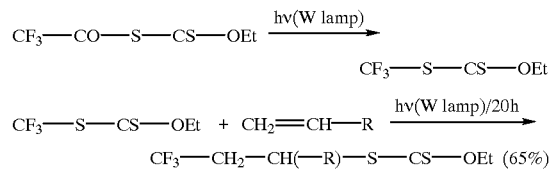

This test produced the expected result, provided that the operation is carried out in two stages. In the first stage the photochemical decarbonylation of the reactant $CF_3COS$—C(S)OEt is carried out and, in the second stage, the resulting product is photolysed in the presence of olefin. The yield of this second reaction is 65%.

What is claimed is:

1. A compound having the formula:

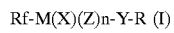

Wherein:

R denotes a carbon-containing radical;

wherein Rf is a carbon-containing radical having at most 20 carbons of formula:

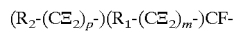

wherein:

$R_1$ and $R_2$, which are similar or different, denote fluorine, chlorine or a carbon-containing radical;

m is zero or an integer chosen within the closed range from 0 to 12;

p is zero or an integer chosen within the closed range from 0 to 12; and

Ξ, which are similar or different, denote a perhalogenated radical, a chlorine or a fluorine atom; with the condition that when m or p are equal to zero, $R_1$ or $R_2$ are electron-withdrawing;

n denotes zero or 1;

M denotes a carbon or a chalcogen heavier than oxygen;

X, and Z, which are similar or different, denote a chalcogen atom; and

Y denotes a sulphur or a selenium atom.

2. A process for the treatment of a compound which has at least one nucleophilic functional group, comprising the steps of contacting at least one nucleophilic functional group with a reactant which is a compound as defined in claim 1, and carrying out a radical reaction of conversion of the compound of formula (I) to a perhaloalkylated thioether in the absence of a substrate.

3. A process for the treatment of a compound which has at least one nucleophilic functional group, comprising the step of contacting said nucleophilic functional group with a reactant having the formula:

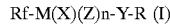

wherein:

R denotes a carbon-containing radial;

Rf denotes a radical of formula:

$(R_2-(C\Xi_2)_p-)(R_1-(C\Xi_2)_m-)CF-$ wherein:
R$_1$ and R$_2$, which are similar or different, denote fluorine, chlorine or a carbon-containing radical;
m is zero or an integer chosen within the closed range from 0 to 12;
p is zero or an integer chosen within the closed range from 0 to 12; and
Ξ, which are similar or different, denote a perhalogenated radical, a chlorine or a fluorine atom; with the condition that when m or p are equal to zero, R$_1$ pr R$_2$ are electron-withdrawing;
n denotes zero or 1;
M denotes a carbon or a chalcogen heavier than oxygen;
X, and Z, which are similar of different, denote a chalcogen atom; and
Y denotes a sulphur or a selenium atom, and reacting the compound (I) by a radical route with at least one substrate having the following formula:

$$R'-S-S-R'' \quad (IV)$$

wherein the radicals R' and R'' of the compound (IV) are identical or different and are of formula (I).

4. A process according to claim 3, wherein the radical route consists of photolysis of the compound (I) having a chromophore group in the presence of the substrate in a reaction mixture optionally including an organic solvent, at a wavelength corresponding to the absorption maximum of the chromophore group.

5. A process according to claim 4, wherein the wavelength is between 200 and 800 nm.

6. A process according to claim 4, wherein the said compound further comprises a solvent having a transparency higher than or equal to 50% at a wavelength corresponding to the absorption maximum of the chromophore group.

7. A process according to claim 6, wherein the wavelength is between 210 and 600 nm and the solvent is acetonitrile, ethanol, butanol, dichloromethane, cyclohexane, cyclopentane, 1,2-dichloroethane, 2,2-dimethylbutane, n-heptane, n-hexane, methanol, 2-methylbutane, isooctane, n-pentane, 2-propanol, 1,2,2-trichlorotrifluoroethane, 2,2,2-trifluoroethanol or a mixture of these.

8. A process according to claim 7, wherein a temperature T$_R$ is provided which is lower than or equal to the boiling temperature, at a given pressure, of the solvent.

9. A process according to claim 8, wherein the compound is a perfluoroalkylated compound and wherein T$_R$ is higher than or equal to 20° C.

10. A process according to claim 8, wherein the compound is perfluoroacylated, and wherein T$_r$ is lower than or equal to 30° C.

11. A process according to claim 3, wherein a thermolysis is being carried out.

12. A process according to claim 11, wherein the said thermolysis is carried out a temperature between 350 and 650° C.

13. A process for the treatment of a compound which has at least one nucleophilic functional group, comprising the step of contacting said nucleophilic functional group with a reactant having the formula:

Rf-M(X)(Z)n-Y-R(I)

wherein:
R denotes a carbon-containing radical;
RF denotes a radical of formula:

$(R_2-(C\Xi_2)_p-)(R_1-(C\Xi_2)_m-)CF-$ wherein:
R$_1$ and R$_2$, which are similar of different, denote fluorine, chlorine or a carbon-containing radical;
m is zero or an integer chosen within the closed range from 0 and 12;
p is zero or an integer chosen within the closed range from 0 to 12; and
Ξ, which are similar or different, denote a perhalogenated radical, a chlorine or a fluorine atom; with the condition that when m or p are equal to zero, R$_1$ or R$_2$ are electron-withdrawing;
n denotes zero or 1;
M denotes a carbon or a chalcogen heavier than oxygen;
X, and Z, which are similar or different, denote a chalcogen atom; and
Y denotes a sulphur or a selenium atom, and reacting the compound (I) by a radical route with at least one substrate selected from the group consisting of alkenes or alkynes which are not functionalized on the unsaturation; ethers or enol esters; enolperhalocarboxylates; vinyl sulfides; enamines; enoxy, enethio or enaminostannanes; allystannanes; enoxy, enethio or enaminosilanes; and allylsilanes.

14. A process according to claim 13, wherein the compound (I)is a thioester and the thioester/substrate molar ratio is between 0.1 and 10.

15. A process for the treatment of a compound which has at least one nucleophilic functional group, comprising the steps of contacting said nucleophilic functional group with a reactant of formula (I):

Rf-M(X)(Z)n-Y-R(I):

wherein:
R denotes a carbon-containing radical;
Rf denotes a radical of formula:

$(R_2-(C\Xi_2)_p-)(R_1-(C\Xi_2)_m-)CF-$ wherein:
R$_1$ and R$_2$, which are similar or different, denote fluorine, chlorine, or a carbon-containing radical;
m is zero or an integer chosen within the closed range from 0 to 12;
p is zero or an integer chosen within the closed range from 0 to 12; and
Ξ, which are similar or different, denote perhalogenated radicals, chlorine or fluorine atoms; with the condition that when m or p are equal to zero, R$_1$ or R$_2$ are electron-withdrawing;

n denotes zero or 1;

M denotes a carbon atom or a chalcogen heavier than oxygen;

X, and Y, which are similar or different, denote a chalcogen; and

Z is oxygen or sulphur; and a source of radicals, and carrying out a thermolysis.

16. A process according to claim 15, wherein the thermolysis is carried out in a tubular reactor made of glass or quartz.

* * * * *